Figure 9:
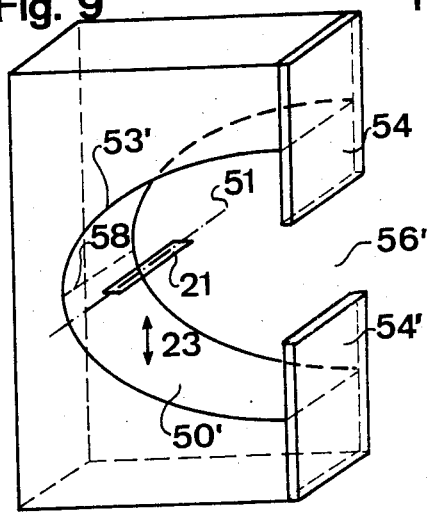

United States Patent [19]

Oehler et al.

[11] Patent Number: 4,657,397
[45] Date of Patent: Apr. 14, 1987

[54] LIGHT COLLECTOR AND ITS USE FOR SPECTROSCOPIC PURPOSES

[75] Inventors: Oskar Oehler, Streulistrasse 24, Zürich; David Sourlier, Zweierstrasse 8, Niederrohrdorf; Alexis Fries, Dietikon, all of Switzerland

[73] Assignees: Oskar Oehler, Zurich; David Sourlier, Niederrohrdorf, both of Switzerland

[21] Appl. No.: 589,087

[22] PCT Filed: Jun. 23, 1983

[86] PCT No.: PCT/CH83/00080
§ 371 Date: Feb. 9, 1984
§ 102(e) Date: Feb. 9, 1984

[87] PCT Pub. No.: WO84/00217
PCT Pub. Date: Jan. 19, 1984

[30] Foreign Application Priority Data

Jun. 25, 1982 [CH] Switzerland .................. 3939/82
May 14, 1983 [CH] Switzerland .................. 2654/83

[51] Int. Cl.⁴ .......................................... G01N 21/31
[52] U.S. Cl. ............................... 356/414; 250/343; 250/353; 350/630; 356/51; 356/432; 356/436
[58] Field of Search ........... 250/342, 343, 345, 353, 250/373; 350/619, 630, 628; 356/51, 317, 318, 414, 436, 437, 440, 442, 432; 362/347

[56] References Cited

U.S. PATENT DOCUMENTS

| | | | |
|---|---|---|---|
| 3,179,898 | 4/1965 | Meltzer | 350/628 |
| 3,745,325 | 7/1973 | Harvey | 350/630 |
| 3,763,348 | 10/1973 | Costello | 350/628 |
| 4,188,542 | 2/1980 | Hogg et al. | 356/39 |
| 4,188,543 | 2/1980 | Brunsting et al. | 250/373 |
| 4,557,603 | 12/1985 | Oehler et al. | 356/418 |

FOREIGN PATENT DOCUMENTS

| | | | |
|---|---|---|---|
| 2104393 | 8/1972 | Fed. Rep. of Germany | 356/317 |
| 793777 | 4/1958 | United Kingdom | 250/353 |

*Primary Examiner*—F. L. Evans
*Attorney, Agent, or Firm*—Roylance, Abrams, Berdo & Goodman

[57] ABSTRACT

The device for collecting the radiation of a light source (20) within a concave mirror comprises a cylindrical or rotationally symmetrical parabolic or elliptical reflector (10'), which is covered with a curved or planar retroreflector (40) having an opening (42). The retroreflector (40) returns part of the light into the vicinity of the source (20) and brings about, due to the partial transparency of this area, that an intense, quasi-parallel light beam can be coupled out through opening (42). After passing through a monochromator element (31), this light can e.g. be supplied to a gas measuring cell (68). The optical efficiency of the device is increased by the concave mirror (57) in a shape supplementing reflector (10', 10''). The measuring signal can be determined by means of a light detector or a microphone (69). In the latter case, an acoustically decoupling gas exchange device is required, which can e.g. be realized by means of capillaries filled with the liquid (75, 75').

39 Claims, 29 Drawing Figures

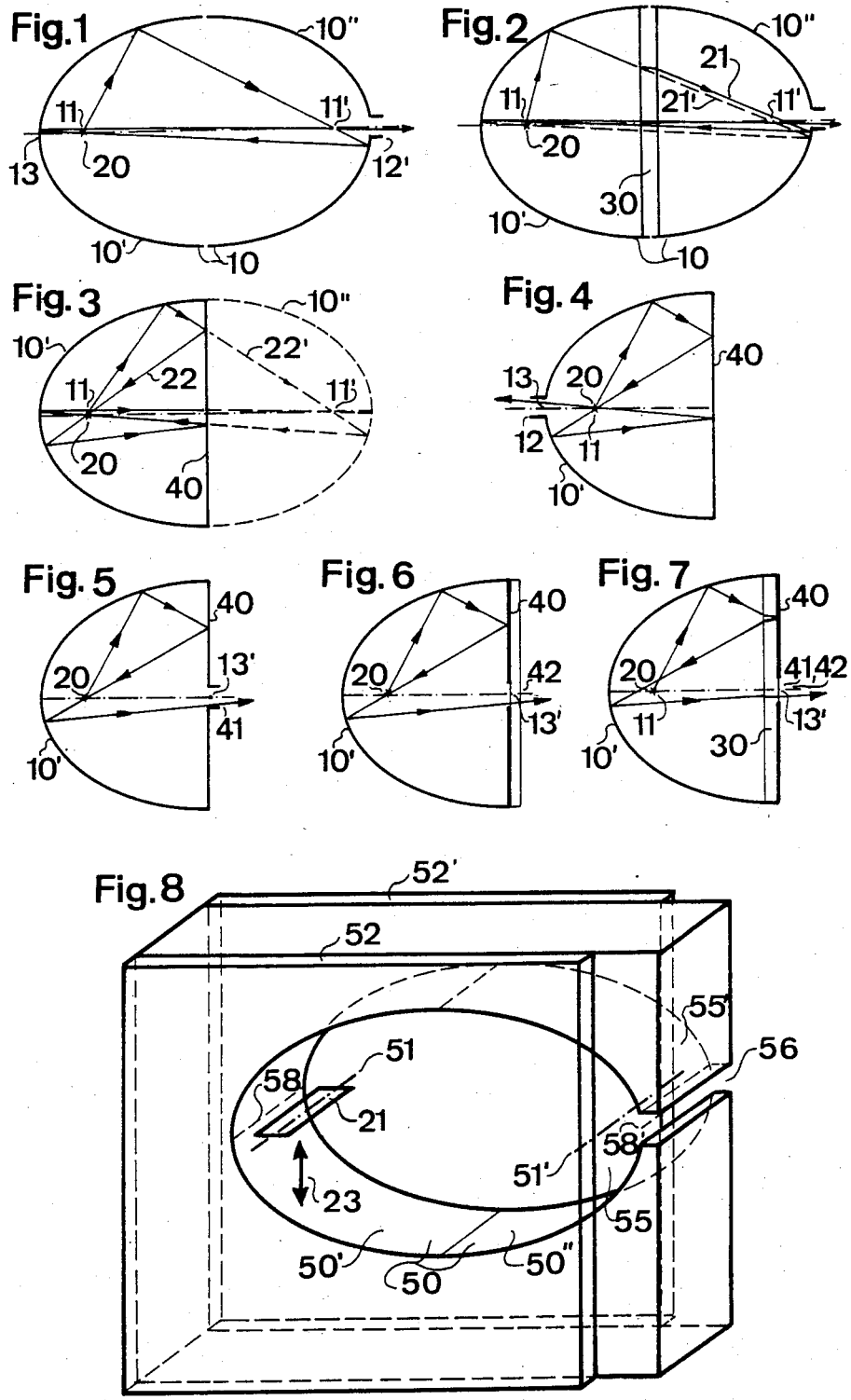

LIGHT COLLECTOR AND ITS USE FOR SPECTROSCOPIC PURPOSES

The present invention is in the fields of geometrical optics and optical spectroscopy. It relates to a device for collecting radiation emanating from a light source within a concave reflector to give a narrow, quasi-parallel beam and the use of said device for optical spectroscopic purposes, particularly for the detection of gases. The invention is based on Swiss Patent Application No. 1,266/81-0 of Feb. 25, 1981, PCT Application No. PCT/CH82/00026 of Feb. 23, 1982 (now U.S. Pat. No. 4,557,603), Swiss Patent Application No. 3939/82-9 of June 25, 1982 and Swiss Patent Application No. 2654/83 of May 14, 1983.

Concave mirrors are known for the purpose of collecting radiation from light sources. In particular, spherical, elliptical and parabolic reflectors are frequently used, particular significance being attached to the two latter devices.

A more detailed description will firstly be given of elliptical concave mirrors. Such reflection devices are very frequently used if the radiation of a small light source is to be focused on a target with a high efficiency level. For this purpose, the light sources and target are arranged in two opposite focal points. A particular use is, for example, the excitation of the ruby laser. One focal point is located in the excitation light source and the other in the ruby rod forming the laser cavity. Reference is made in this connection to the book by B. A. Lengyet, entitled "Lasers", Wiley Publications, 1971. In this application use is made of the fact that any beam emanating from one focal point, occurs in the other focal point following reflection. Thus, a very considerable efficiency of the radiation intensity transmission can be achieved. However, the light bundle is very divergent, if radiation is collected from a large solid angle. It is often not possible to accept this divergence, e.g. if the light is to be dispersed in a monochromator.

The efficient formation of a quasi-parallel beam by means of an ellipsoidal reflector is described in Swiss Patent application No. 1,266/81-0. Not only a single reflection on the ellipsoidal concave mirror is observed and instead it is assumed that, after a second reflection on the reflector surface, the light is again returned into the source and partially penetrates the latter. Thus, the ellipsoidal surface has the double function, on the one hand as a reflector which conducts the light of the source located in one focal point into the other focal point and on the other hand as a retroreflector which again returns the radiation to the source. The light collection is based on the fact that all the light beams emanating from a focal point with increasing numbers of reflections on the ellipsoidal mirror surface and light source penetrations asymptotically approach the large major axis. Thus, there is a light collection along this axis. The beam is coupled out through a small opening of diameter D, provided in the extension of this large major axis A. Tests were carried out on a prolate ellipsoid of revolution, i.e. for the case where A is simultaneously the rotation axis and consequently the two other major axes have the same length B. For $A/B=1.2$ and $D/B=0.1$, it was found that 30% of the light of a filament arranged in a focal point could be coupled out, the emitted light being within a cone of 15°.

A disadvantage of this construction is that the light beam must in each case after 2, 4, 6 ... reflections penetrate the light source provided in a focal point. Due to the incomplete transparency of the light source, which in the case of a filament is approximately 70%, the efficiency of the light collector is reduced.

Moreover, the geometrical dimensions of the device must be made very large, because a good luminous efficiency is only ensured if the dimensions of the reflector are large compared with those of the radiation source.

It is often desired to concentrate the light radiation on a small circular or square surface, for example onto the light-sensitive surface of a photo-detector. The problem occasionally arises of illuminating a linear extended element, for example a slit diaphragm. In the latter case, the aforementioned rotationally symmetrical reflector devices do not constitute an optimum solution with respect to the luminous efficiency.

The aforementioned light collimation process presupposes a partially transparent radiation source. A source with this charcteristic can be very satisfactorily realised by a filament. As the efficiency of the reflector drops to a considerable extent for a lateral displacement of the light point out of the focus, the filament must be kept very thin and must be precisely adjusted in the ellipsoid major axis. However, the required thinness of the filament constitutes a decisive restriction to its electrical loading capacity and therefore also a restriction to the luminous efficiency of the source.

The positioning of the filament along the major axis corresponds to an adjustment in two dimensions, a requirement which represents a considerable effort.

In certain applications, a narrow and preferably parallel light beam is often desired. On the basis of a small light source, a parallel beam can be produced in that the source is positioned at the focus of a parabolic reflector.

If a good parallelism of the beam is required, then the dimensions of the reflector must be large compared with those of the light source. However, this means, particularly if a high luminous efficiency is additionally required, that the parallel beam has a large cross-section, so that the luminance of the light beam is low.

Gases, particularly those with a low atomic number, such as CO, $CO_2$, $CH_4$, etc can be reliably and selectively detected with optical spectroscopic methods because they very specifically absorb the light in the infrared spectral range.

Two fundamentally different methods can be used for the optical spectroscopic detection of gases, on the one hand the extinction method and on the other the photoacoustic method.

The former is based on the determination of the light attenuation in the sample gases. It is absolutely necessary in such a measurement that the intensity of the light beam is very accurately known before it enters the absorption cell, because the concentration determination takes place from the difference of the light intensity of the wavelength specific for the gas before and after the light absorption path. Thus, conventionally, part of the light is coupled out by auxiliary optics, e.g. a semireflecting mirror. However, this requires additional material and adjustment expenditure.

In order to ensure a long light path and therefore to achieve a considerable attenuation of the beam, despite restricted dimensions of the measuring device, cells are often used for extinction measurements on gases in which the light is reflected backwards and forwards a number of times, i.e. so-called multiple reflection cells. In such a cell it is on the one hand necessary that the incident light beam is bundled in a narrow manner, it being possible to counteract the divergence of the beam by a special mirror shape, whilst on the other hand the mirror system must be very accurately adjusted. Thus, as a rule, multiple reflection cells are very complicated. A further important disadvantage of multiple reflection cells is the ageing of the optical system, i.e. the fact that over a period of time the light reflectivity changes and the geometry can become misadjusted. Such changes lead to intensity attenuations which, if calibration measurements are not frequently carried out, cannot be differentiated from the sample gas-caused signal attenuation.

The second optical spectroscopic gas detection method is suitable for the detection of low concentration atmospheric gas impurities, such as carbon monoxide, nitric oxide or methane. It is a photoacoustic gas detection method. Thus, the pressure changes occurring in a gaseous mixture on absorbing monochromatic light (mainly infrared radiation) by a gaseous component are detected by a microphone, such as is described in the article by L. G. Rosengren, Applied Optics, Vol. 14, p. 1960, 1975. For this purpose, mainly intense, matchable infrared lasers are used together with highly sensitive capacitor microphones.

The fact that the main components of air, namely nitrogen, oxygen and argon, within the framework of the dipole approximation, do not absorb infrared radiation has an unfavourable influence in this connection. For example, as described in J. Appl. Physics, Vol. 42, p. 2934, 1971, L. B. Kreuzer was able to detect methane in nitrogen, corresponding to a concentration of 10 ppb ($10^{-8}$) with the aid of a 16 mW laser. It has often been surmised that when using intense infrared laser radiation concentrations of up to $10^{-13}$ can be measured.

When the demands concerning the sensitivity of the gas detection are much less stringent, it is possible to greatly simplify the detection system. In particular, the expensive matchable infrared laser can be replaced by a simple system comprising an incandescent body and a narrow band interference filter. Recently, M. J. D. Low and G. A. Parodi have described in Infrared Physics, Vol. 20, p. 333, 1980, an infrared spectrometer based on the optoacoustic effect, in which an incandescent pin is used in place of a laser. However, due to its limited intensity, this source has not proved satisfactory for an optoacoustic infrared spectrometer when combined with a grating monochromator.

An important advantage of the photoacoustic method is that the light source intensity is directly included as a proportionality factor in the magnitude of the photoacoustic signal. Thus, the gas concentration measurement does not take place from an intensity difference measurement, as with the extinction method.

However, when high demands are made on the stability of the detection sensitivity, it is advisable to monitor the light source intensity.

Monochromatic light radiation is an absolute requirement for achieving a selective gas detection by means of optical spectroscopic methods. This requirement is fulfilled from the outset when using laser light sources (but the undesired modes must be eliminated). However, the installation of a prism grating or interference filter monochromator is unavoidable if a broad band, e.g. thermal light source is used.

From the intensity standpoint, the replacement of the grating monochromator by an interference filter leads to advantages, but these are gained at the cost of flexibility and precision.

The requirements regarding the divergence of the light beam are not too high when using interference filters. To avoid undesired changes to the band pass characteristics of the interference filter, the half-aperture angle of the light bundle should be below 15 angular degrees.

In order to eliminate electronic drift phenomena, optical spectrometers are generally operated with intensity-modulated light sources. Generally, the light intensity is mechanically modulated with the aid of a rotary sector disk. However, such light interrupters are relatively expensive and fault-prone.

As inexpensive detectors (e.g. pyroelectric elements and photoacoustic cells) can often be operated in an optimum manner at low frequency, the light source can often be thermally modulated without using a mechanical light interrupter. This solution is particularly favourable for a simple, reliably operating gas detection system.

A correct gas concentration determination requires that it is possible to satisfactorily scavenge the cell before or during the measurement. In the case of an identical sample gas and light detection cell, as applies with photoacoustic methods, the measurement during the gas exchange is problemmatical due to the unavoidable flow-caused pressure and temperature fluctuations. However, this problem can be overcome when working at high modulation frequencies.

However, in the case of a thermal and therefore low frequency modulation, an alternating scavenging—measuring process is unavoidable. This means that valves are necessary, which control the gas flow. However, in the case of photoacoustic cells the demands made on these valves are low, because the photoacoustic pressure signal is very small, being in the mPa range. Electromagnetic valves, such as are used for pneumatic purposes, are therefore used in an optimum manner with the set requirements, with respect to price, dimensions and complications.

Whilst avoiding the aforementioned disadvantages, the problem of the invention is to provide a device for the efficient collection of the radiation of a light source within a concave reflector so that it is formed into a narrow, quasi-parallel bundle, which is suitable for optical spectroscopic purposes, particularly for the detection of gases.

This problem is solved by the arrangement of a small spot-like light source in one of the two focal points of a closed rotary ellipsoidal reflector and the coupling out of the beam formed through a hole in the direction of the extended large major axis of the ellipsoid. A light-refracting body within the ellipsoid ensures that a large part of the radiation is returned into the light source after multiple reflection. The dimensions of the ellipsoidal reflector are reduced in that the reflector is formed by an ellipsoidal hemisphere instead of by a full or solid ellipsoid, whilst the retroreflector is constituted by a flat mirror. The beam formed is either coupled out through an opening in the direction of the large major axis of the ellipsoidal hemisphere or through an opening in the centre of the flat mirror.

The problem can also be solved by arranging a filament or strip-like light source in the vicinity of one of the two focal lines of a closed cylinder with an elliptical base or at the focus of an elliptical half-cylinder, which is partially covered by a flat mirror.

Instead of by means of a rotary ellipsoid or an elliptical cylinder, the problem can also be solved with the aid of a rotary paraboloid, which is partially covered by a flat mirror, or a cylinder with a parabolic base partially covered by a flat mirror. The light source is located at the focus of the paraboloid, or at the focal line of the parabolic cylinder. The coupling out of the light from the optical device takes palce through an opening, or a transparent region in the central area of the flat mirror.

The necessary intensity modulation can either be produced directly by controlling the luminous body current, or mechanically with the aid of a rotary sector disk. The monochromator is, for example, constituted by an optical narrow band—band pass filter, preferably an interference filter. However, several optical filters can be arranged on a rotary disk, which simultaneously, e.g. fulfils the function of the light modulator.

The light intensity measurement is carried out either by non-gas-selectively functioning detectors, e.g. a pyroelectric element or a photoacoustic measuring cell, which contains a measuring gas.

In the latter case, the efficiency of the gas detection can be improved by providing a mirror on the back of the photoacoustic cell.

If the gas measuring cell is operated at low frequency, then it must be acoustically separated from the ambient during the measurement. This takes place by means of narrow capillaries or sintered bodies in the cell wall, by simple mechanical valves, or by using a non-linear flow system based on hydrodynamic principles and whose function is like that of a Schmitt trigger. A feed means, essentially based on a small loudspeaker is used for the forced gas circulation.

The invention is described in greater detail hereinafter relative to the drawings, wherein show:

FIG. 1 a sketch of the full ellipsoidal reflector explaining the principle.

FIG. 2 a possible construction of the full ellipsoidal reflector with a light-refracting body according to the invention.

FIG. 3 a sketch of the ellipsoidal hemisphere with a flat mirror according to the invention.

FIGS. 4, 5 and 6 the coupling out of light from the ellipsoidal hemisphere.

FIG. 7 an ellipsoidal hemisphere with a flat mirror, whose back is partly silvered.

FIG. 8 a sketch of the elliptical full cylinder with a light source and beam coupling-out slit according to the invention.

FIG. 9 a sketch of the elliptical half-cylinder with flat front cover mirrors forming the beam exit slit and a light source according to the invention.

Figure 10:
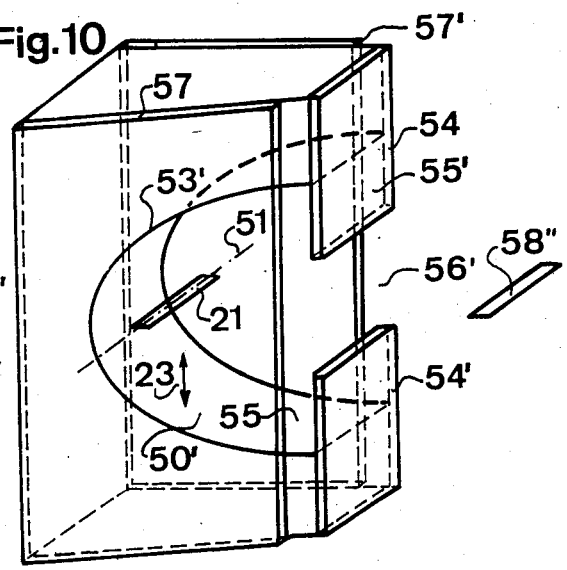

FIG. 10 a sketch of the elliptical half-cylinder with flat front cover mirrors forming the beam exit slit, lateral cover mirrors and light source according to the invention.

Figure 11:
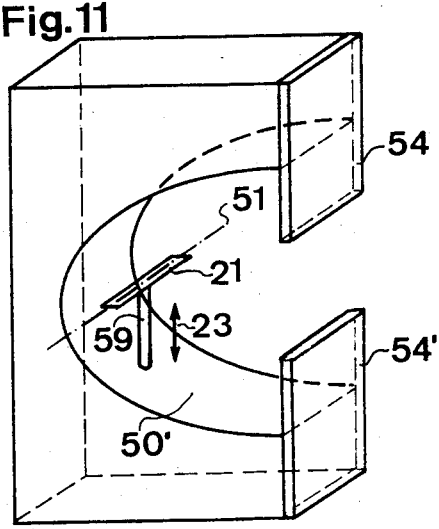
Figure 12:
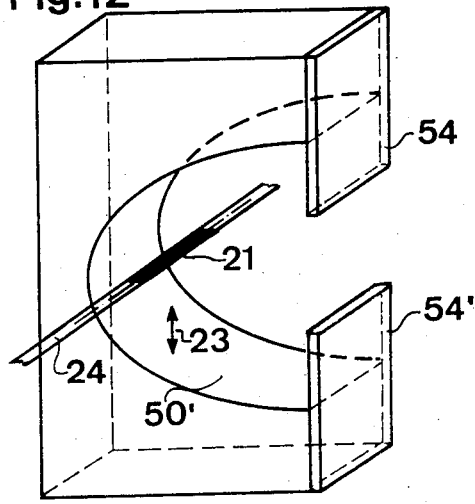

FIGS. 11 and 12 examples of possible mounts for the light source.

Figure 13:
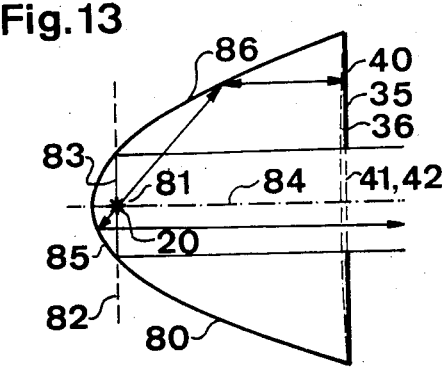

FIG. 13 a sketch of the partly covered rotary paraboloid according to the invention.

Figure 14:
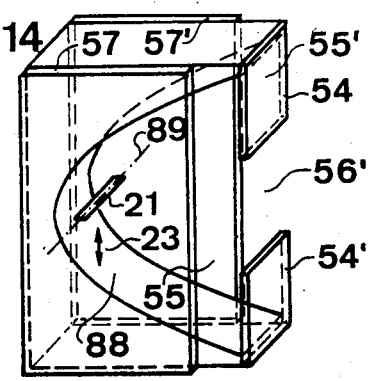

FIG. 14 a sketch of the partly covered parabolic cylinder according to the invention.

Figure 15:
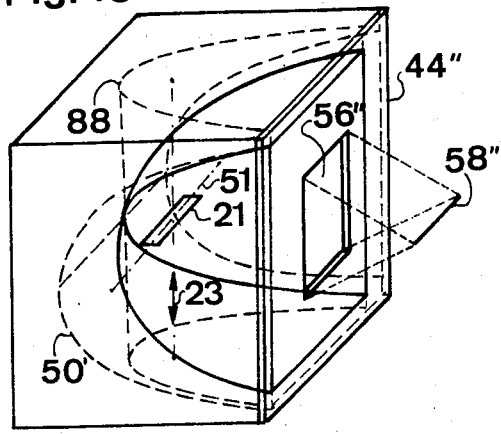

FIG. 15 a sketch of the combined elliptical—parabolic cylinder.

Figure 16:
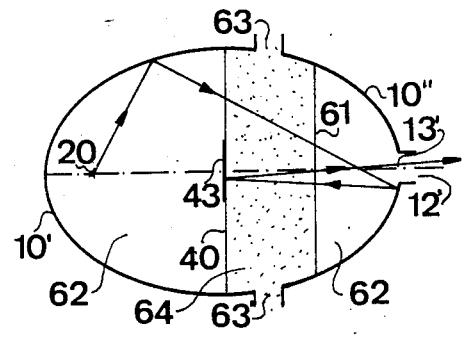
Figure 17:
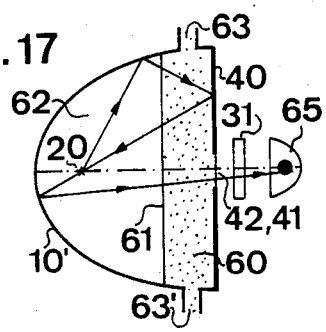

FIGS. 16 and 17, uses of the ellipsoidal reflector as a multiple reflection gas measuring cell.

Figure 18:
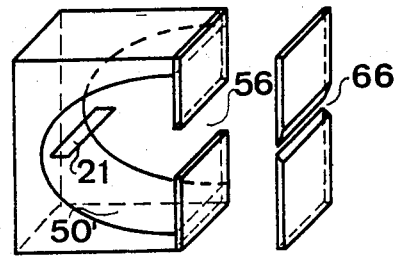

FIG. 18 possible use of the reflector device according to the invention for illuminating the entrance slit of an optical device, e.g. a monochromator.

Figure 19:
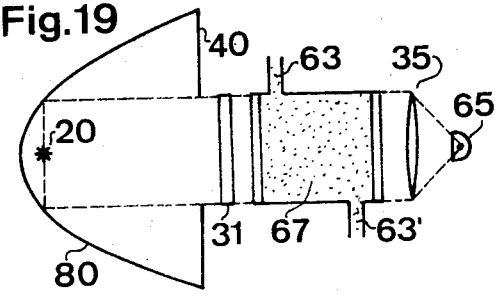

FIG. 19 use example for the partly covered rotary paraboloid for detecting gases by means of the optical extinction method.

Figure 20:
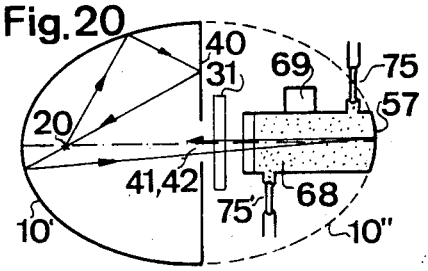

FIG. 20 use of the ellipsoidal reflector for the photoacoustic detection of gases.

Figure 21:
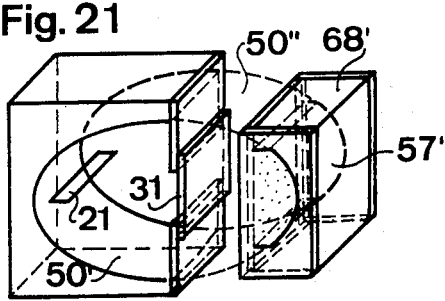

FIG. 21 further use of the reflector device according to the invention for coupling in light in a photoacoustic cell.

Figure 22:
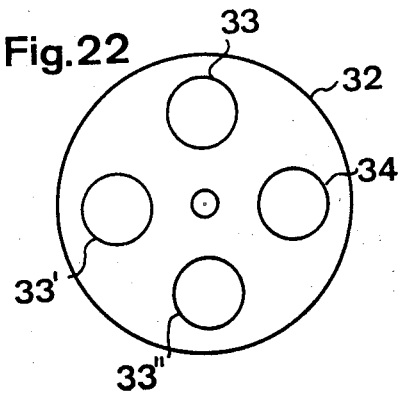

FIG. 22 possible embodiment of a combined monochromator-light interrupter.

Figure 23:
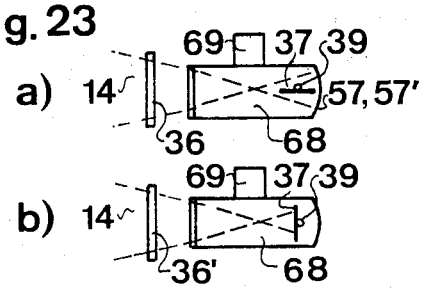

FIG. 23 possible construction of a cell for the combined photoacoustic measurement of the gas concentration and the light source intensity by means of a mechanical device.

Figure 24:
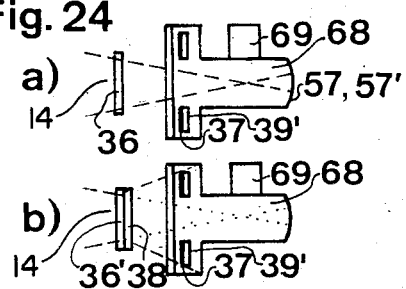

FIG. 24 further possibility for the combined photoacoustic gas concentration and light source intensity measurement by means of an optical device.

Figure 25:
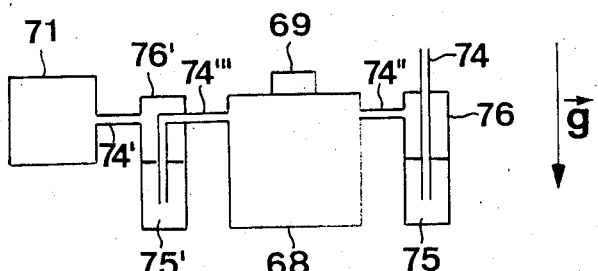

FIG. 25 a photoacoustic cell with acoustic liquid confining.

Figure 26:
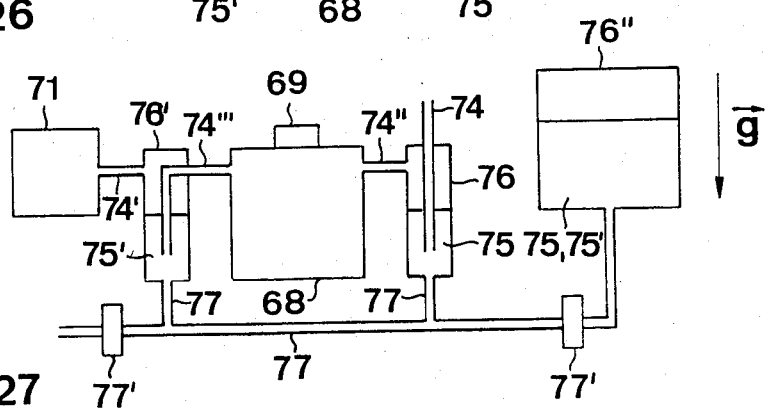

FIG. 26 construction according to FIG. 25, with additional liquid exchange device.

Figure 27:
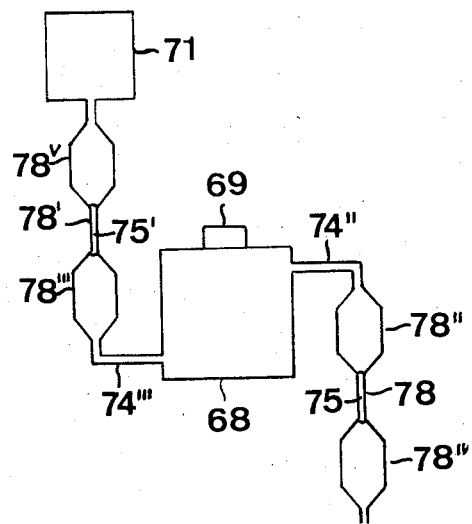

FIG. 27 photoacoustic cell with acoustic stopping by means of liquid-filled capillaries.

Figure 28:
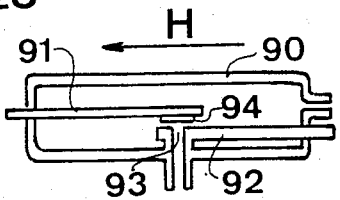

FIG. 28 an example of a magnetomechanical device for acoustic decoupling of the photoacoustic cell.

Figure 29:
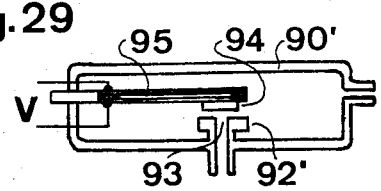

FIG. 29 example of an electromechanical device for acoustic decoupling of the photoacoustic cell.

In the representation of FIG. 1 is shown the full ellipsoidal reflector, as described in Swiss Patent Application No. 1,266/81-0 of Feb. 25, 1984 and PCT Application No. CH 83/00026 of Feb. 23, 1982. In accordance with the laws of geometrical optics, a light beam emanating from the focal point 11 of an ellipsoid according to FIG. 1 passes into focal point 11' after reflection on the reflector wall. Conversely, the ellipsoid also acts as a retroreflector by returning to the origin 11 the beam which has passed through focal point 11'. Thus, assuming complete transparency of the source, the light is reflected backwards and forwards between the two focal points 11, 11'.

On following such a light beam, it is found that with increasing numbers of reflections on the ellipsoidal surface it rapidly approaches the large ellipsoidal major axis. A light source 20 arranged in one of the two focal points therefore produces a very intense and ideally parallel light bundle in the large major axis.

This light bundle can be coupled out through a small opening in one of the intersection points of the large major axis and the ellipsoidal surface (e.g. at 12' in FIG. 1). However, as a result of the finite size of opening 12', a beam can leave the reflector system 10, before falling in the large major axis. This is responsible for the formation of a light cone, whose opening angle is determined by the diameter of this opening on the one hand and the ellipsoidal parameters on the other.

It is important that the rear area 13 of reflector surface 10' facing opening 12' has a good reflectivity and is not covered by the light source mount.

However, this device completely fails to function in the ideal case, when the light source is precisely punctiform with optimum emissivity and is precisely located in a focal point of an imperfect ellipsoid. All light emitted by the source is returned to it after two reflections, where it is absorbed. It is realistic to use a filament-like light source with considerable transparency and negligible dimensions. The light reflected back onto the filament is not lost and in fact brings about an additional heating of the incandescent body. However, the incomplete transparency of the light source leads to a reduction in the luminous efficiency. Thus, in the case of a 3 mm long filament, whose radiation was coupled out through a 1 cm opening of a rotary ellipsoid with major axis lengths of 14.4 and 12 cm, a luminous efficiency of 30% was found, whereas more than 50% was expected on the basis of a computer simulation.

The essence of the invention is that the light beam 21 is slightly deflected by a light-diffracting body 30, as shown in FIG. 2, so that after two reflections it is no longer returned to the source. The light-refracting body can e.g. comprise a flat disk 30, which is fitted in the centre between the two focal points 11, 11', as shown in FIG. 2. The advantages of this arrangement are shown by a corresponding computer simulation. The original, undeflected beam 21', as would be present without the light-refracting body 30, is indicated by an interrupted line, whilst the beam 21 broken by 30 is characterized by a continuous line. When dimensioning the light-refracting body, it must be ensured that the light deflection is only small, because otherwise the light collecting action of the ellipsoid would be greatly reduced.

FIG. 3 shows the ellipsoidal hemisphere 10' which reduces the geometrical dimensions with a flat retroreflector 40. The operating principle of this arrangement is precisely the same as the full ellipsoidal reflector shown in FIG. 1. For illustration purposes, the missing ellipsoid half 10' is indicated by a broken line. The flat mirror surface coincides with the median normal plane of the two focal points 11, 11'. Thus, the beam path and also the light collecting effect along the large major axis is the same as in the case of the full ellipsoid. This is immediately apparent by the drawn-in beam 22 and its virtual supplement 22', shown by the broken line.

It is a disadvantage of the hemisphere according to FIG. 3 compared with the full ellipsoid of FIG. 1, that it is always necessary for the focal point 11 containing the light source to penetrate, which leads to a light attenuation as a result of the incomplete transparency thereof. There is also an additional reflection, namely that on the retroreflector 40. However, the two disadvantages are partly compensated in that a large part of the beams makes do with a reflection less on the ellipsoidal surface in order to be coupled out under a given angular cone. Thus, as a function of the ellipsoidal parameters an even greater luminous efficiency is obtained than in the case of a full ellipsoid.

The coupling out of the complete beam either takes place through an opening 12 in the ellipsoidal hemisphere as shown in FIG. 4, and as with the opening 12' of FIG. 1, or through an opening 41 in the centre of the flat mirror surface 40 according to FIG. 5. As is shown in FIG. 7, the light bundles 41 can also be removed through a non-reflecting, transparent central area 42 in the flat retroreflector surface 40 of light collector 10', 40 instead of through opening 41.

An important advantage results from the coupling out of light through 41 or 42 of the flat mirror surface 40, as shown in FIGS. 5 and 6, instead of through the opening 12' or 12 in ellipsoidal surface 10'' or 10' of FIGS. 1 and 4. As the focal point 11' is located outside the light collector, it can e.g. be moved into the device to be irradiated, as is shown by FIGS. 17 and 20. Thus, a high light intensity can be obtained in the irradiated object. This leads to a convergent, instead of a divergent beam at the exit opening. A combination of the beam deflection by a light-reflecting body 30 according to FIG. 2 (for preventing light absorption by the source) and the flat mirror surface according to FIG. 3 is shown in FIG. 7. The flat mirror surface 40 is externally completely or partly silvered. This makes it possible to utilize both the light-refracting and the reflecting property of said body. The coupling out of light can take place through an opening 41 or a non-reflecting central area 42 of said surface 40, as shown in FIG. 7, or through an opening 12 in the ellipsoidal surface in the same way as in FIG. 4.

The rotationally symmetrical ellipsoidal hemisphere 10' covered with a flat mirror 40 and with coupling out of light in the central area 41 of mirror 40, as shown in FIG. 5, has a very high luminous efficiency. Thus, in accordance with computer simulations, it was experimentally confirmed that there is a luminous efficiency of approximately 60% for a 0.7 mm long filament having a diameter of 0.75 mm, located at the focal point 11 of a rotationally symmetrical hemiellipsoidal reflector 10', 40. The length of the large axes is $A=B/2=40$ mm and the diameter of the light transmission area in the flat mirror 40 is $D=20$ mm. The calculations are based on the following experimentally determined values: spherical surface reflectivity 71%, flat mirror reflectivity 95% and filament transmission 65%. The prerequisite for obtaining such a high luminous efficiency is the small size of the source compared with the reflector. As the maximum electrical loading capacity and consequently the attainable light emission, apart from the material constants, results from the filament surface, the effective luminous efficiency is low. The elliptical normal cylinder 50 shown in FIG. 8 has certain advantages compared with the rotationally symmetrical reflector 10. However, doing away with rotational symmetry constitutes a reduction in the luminous efficiency, which can admittedly be improved in that the elliptical cylinder 50 is covered on both sides by flat mirrors 52, 52', as shown in FIG. 8. However, it was not possible to achieve the high efficiency of the rotationally symmetrical reflector.

The question therefore arises as to what advantages can be provided by the cylindrical reflector. Both measurements and computer simulations have shown that in the case of the rotationally symmetrical reflector, the light source must be very precisely positioned on the rotation axis 14 of FIG. 1, as otherwise there is a great reduction in the efficiency. However, the source position dependence of the efficiency is less marked in the case of a displacement of the source along the axis. However, this means that in particular the diameter of the filament must be kept small and must be very accurately adjusted in the rotation axis. In the case of the proposed elliptical cylinder 50, it is possible without significantly reducing the efficiency, to construct the light source as a rectangular strip 21, as shown in FIG. 8. This makes it possible to give the light source a considerable extension, which makes it possible to obtain an increased light intensity.

Another advantage of the proposed reflector is that the light source need only be accurately adjusted in a single dimension, namely in the direction parallel to the small ellipse main axis, as indicated by arrow 23 in FIG. 8.

In the same way as with the rotary hemiellipsoid of FIG. 3, it is also appropriate to use only half of the elliptical cylinder, cf FIG. 9. Two planar retroreflectors 54, 54' are made to coincide with the normal plane of the focal points of the ellipse 53' forming the normal cylinder 50'. These retroreflectors have the same function as retroreflector 40 in the rotationally symmetrical hemiellipsoidal reflector 10' of FIG. 3, namely the retroreflection of the beam in the focal line 51 containing light source 21. The two flat mirrors 54 54' are positioned in such a way that a slit 56', ensuring the coupling out of the light is left free. For this purpose, slit 56' must be located in the vicinity of the plane of symmetry, which is formed by the large major axis of ellipse 53' and the cylinder axis.

The two flat retroreflectors 54, 54' can also be replaced by a single flat mirror, which centrally has a transparent region corresponding to slit 56'.

The two laterally positioned flat mirrors 57, 57', as shown in FIG. 10, are used for increasing the luminous efficiency, by reflecting back into the reflector the laterally escaping radiation. Optically, they correspond to an extension of the cylinder to infinity. The flat mirrors 57, 57' can either be arranged in parallel or can slope towards one another, as shown in FIG. 10. As a result of the lateral flat mirrors, light under a large divergence angle can pass into the focal region 58''. This is important when using optical filter elements utilizing the interference effect, because changes can occur in the band pass characteristic. Although leading to a reduction in the luminous efficiency, this can be obviated in that the two flat mirrors 57, 57' do not extend right up to the front against the retroreflectors 54, 54', so that light which would be coupled out under a large emergence angle through opening 56' prematurely leaves the optics through slit 55 or 55' (cf FIG. 10). The incomplete covering by flat mirrors 52, 52', whilst leaving slits 55, 55' free, is also appropriate in the case of the elliptical full cylinder 50, as shown in FIG. 8. The value of the elliptical cylindrical reflector according to FIG. 10 was checked by means of a computer simulation. Whilst assuming a strip-like light source of dimensions 8×4×0.5 mm, a rotationally symmetrical hemiellipsoidal reflector according to FIG. 5 with dimensions A/2=24 mm, B=40 mm and a hole diameter in the flat mirror of 20 mm gave a luminous efficiency of 40%. For the same light source and the same ellipse parameters, a slit width of 20 mm and a cylinder height of 30 mm, the elliptical cylinder according to FIG. 10 gave a luminous efficiency of approximately 60%.

FIGS. 11 and 12 show examples of possible mounts for light source 21. A lateral mounting support for the source, as shown in FIG. 11, is e.g. advantageous. The lateral support 59 leads to smaller efficiency losses than in the case of a mount in the rear part of the elliptical cylinder, i.e. in the light collimation region. In addition, the luminous efficiency can be varied by means of support 59 through a displacement in the longitudinal direction 23 in the only critical dimensions and consequently the light source is adjusted. In FIG. 12, the strip-like light source 21 is in lateral form (24). In the case of this mount, it must be ensured that a good adjustment in the direction shown in FIG. 12 can be ensured.

It is often desirable for the light radiation to be focused directly and efficiently on a small spot, e.g. on the light-sensitive area of a detector. However, it is occasionally desirable to collect the radiation into a narrow parallel beam beforehand. As a result of the laws of geometrical optics and on the basis of a punctiform light source, it is possible to produce a parallel beam if the source is located in the focus of a parabolic reflector. However, a high radiation density cannot be achieved with such devices. An improvement can be obtained through the modified parabolic reflector 80, as shown e.g. in FIG. 13. In the same way as with the optical devices of FIGS. 1 to 12, the increase in the light collection is due to the use of a retroreflector 40, which returns to the source part of the emitted radiation. A partial transparency of the source is once again important for the operation of this device.

The rotary parabolic mirror 80 of FIG. 13 is e.g. covered by the flat retroreflector 40, in whose centre is provided a circular disk-shaped opening 41 or a corresponding light-transparent region 42. The size of this circular disk 41, 42 coincides with disk 83, cut from an orthogonal plane 82 to rotary axis 84 arranged in focus 81 through the rotary paraboloid 80.

The light emanating from source 20 falls in the rear part 85 of paraboloid 80 with respect to the normal plane 82 and is coupled out from the reflector system 80, 40 through opening 41, 42 parallel to the rotation axis 84. The part of the radiation falling in the front part 86 of the parabolic reflector 80, firstly reaches the flat retroreflector 40, from where it is returned on the same light path into source 20 after reflection on the parabolic surface. It partly passes through source 20 and finally reaches the rear part 85 of the parabolic reflector, from where the light is coupled out through opening 41, 42 as a parallel beam to rotary axis 84.

In the case of the covered hemiellipsoidal reflector, as shown in FIG. 3, the light emanating from source 20 firstly falls on the retroreflector 40 and is collected in the same way as the proportion firstly reaching the ellipsoidal surface 10'. This is linked with the fact that the elliptical optics is virtually supplemented by retroreflector 40. Thus, with the aid of the covered hemiellipsoidal reflector, a very high light collection efficiency is achieved. Such a good result cannot be achieved with the covered parabolic reflector, as shown in FIG. 13. The light, which emanates from source 20, falls directly onto flat mirror 40, is no longer returned to the focal point and can consequently provide no proportion of the parallel beam. Thus, the radiation portion must be looked upon as an uncontrolled loss. The reason for this disadvantage is immediately apparent, because the joining together of two paraboloids as results from the virtual supplementing of reflector 80 by retroreflector 40, is of little use for beams falling from a focal point 81 onto the other paraboloid reflector half.

It has been assumed that the external diameter D of flat mirror 40 is twice as large as the diameter of the disk cut from the paraboloid through the normal plane 82 containing the focal point 81. It has also been assumed that the reflectivity of parabolic reflector 80 is 69% and that of the flat retroreflector 40, 95%, so that the light source 20 has a transparency of 65%. Under these conditions and compared with the uncovered reflector, an increase in the radiation density in the parallel beam of 30% is expected.

A slight increase in the efficiency of the optics can be achieved in that, in the same way as with the arrangement of FIGS. 2 and 7, a light-refracting body is provided in the interior of the reflector means, which slightly deflects the light beam. Thus, the beam no longer returns precisely into light source 20, where it was partly absorbed and instead moves just past it. Unlike in the case of the ellipsoidal reflector 10, the deflection cannot be achieved by a plane-parallel plate 30, because the beams returned to the light source region always strike the flat retroreflector 40 in a vertical manner. The desired deflection can however, be achieved by a body 35 with a curved surface 36, as shown by the broken line in FIG. 13. The retroreflector 40 can be constituted by a slightly curved mirror, which represents an alternative solution with a similar action.

FIG. 14 shows an analog to the covered elliptical cylinder of FIG. 10. Reflector 88 is constructed as a parabolic cylinder. The latter is either covered by two flat mirrors 54, 54' forming the retroreflector, or by a single flat mirror with an opening or a transparent recess in the central region 56'.

The two laterally fitted mirror surfaces 57, 57', which as flat mirrors are either parallel or oblique to one another, or can have a curvature, are used for increasing the efficiency of the optics, in that they return to the reflector the laterally escaping radiation. If flat mirrors are used as the lateral reflectors 57, 57', the light beam passing out of opening 56' is located in a parallel plane to the plane formed by the parabola and cylinder axis, but not in an orthogonal plane to the cylinder axis.

If it is to be ensured that the radiation cannot escape under an excessively oblique angle, then the lateral reflectors 57, 57' should not be extended forwards up to retroreflectors 54, 54'. Beams which would pass through opening 56' under a very oblique angle can prematurely escape through the lateral slits 55, 55'.

The parabolic cylinder of FIG. 14 has a lower efficiency than the covered rotary paraboloid of FIG. 13. The advantage of the parabolic cylinder is that the light source 21 can be constructed and arranged in filament or strip-like manner parallel to focal line 89. It can therefore have a larger surface than the source in the case of therotationally symmetrical analog of FIG. 13.

The only critical adjustment direction of light source 21 is indicated by arrow 23 in FIG. 4 and runs parallel to the parabola and cylinder axis.

Reference is made to FIGS. 11 and 12 in connection with the mounts for the light source 21 and these apply in connection with the parabolic cylinder, in the same way as for the elliptical cylinder.

In connection with the description of FIGS. 8, 10 and 14, it was assumed that the two lateral reflectors 52, 52' or 57, 57' are planar. However, it is also conceivable to use curved mirrors.

Therefore, it is very appropriate to e.g. use an arrangement in which the cylinder has an elliptical shape 50', as shown in FIG. 9, whilst the two lateral reflectors 57, 57' approximate a parabolic cylinder 88, cf FIG. 15. As a result, the light is collected to a laterally substantially limited focal line 58''. The elliptical shape is responsible for the focusing to a focal line and the parabolic cylinder shape of the lateral reflectors 57, 57' is responsible for the parallelism of the radiation to the orthogonal plane of focal line 51 of the elliptical cylinder. The retroreflector 44'' is advantageously constituted by a flat mirror with a rectangular central opening 56'' or a corresponding transparent area, as shown in FIG. 15. However, the transition from the elliptical to the parabolic cylinder orthogonal thereto can be made continuous.

Reference will be made hereinafter to the use of the devices of FIGS. 1 to 15 for optical spectroscopic purposes. Particular importance is attached to the optical detection of gases (reference being made in this connection to PCT Application No. CH82/00026 of 23.2.1982), although it is naturally also possible to investigate liquids and solids, as well as their interfaces.

FIGS. 16 and 17 show possible uses of the ellipsoidal reflector of FIGS. 2 and 3 for the detection of gases. The reflection devices are designed as combinations of light collectors and multiple reflection gas absorption cells.

FIG. 16 shows a full ellipsoidal reflector, in whose one half 10' is located light source 20 and in whose other half 10'' is located the measuring gas-containing area 64, which is separated from the remaining reflector space 62 by surfaces 40 and 61. Both 40 and 61 are transparent for the wavelengths which are important for gas detection, a reflecting area 43 being provided in the centre of the flat retroreflector surface 40. As a result, during the collection process, the light remains trapped in the ellipsoid half 10'' containing the measuring gas and is no longer attenuated on passing through light source 20. The coupling out of the light takes place through opening 12'. There is also no need for partition 61. The function of the latter is merely to keep impurities which, during measuring gas exchange, can pass through the opening 63, 63' into measuring gas area 60 away from the reflector zone important for the reflection (around the light coupling-out opening 12').

In FIG. 17, the measuring gas is e.g. located in an intermediate area, which is kept separated from the light source area 62 by partitions 40 and 61. Gas exchange takes place through openings 63 and 63'. The partition 62 is transparent for the radiation of the wavelength important for gas detection, whilst the flat partition 40 is silvered and is provided centrally either with an opening 41 or a transparent region 42. However, partition 61 can be omitted, but it is then necessary to accept gas flow-caused intensity fluctuations of the light source.

The light passing out of the transparent region 41, 42 of 40 is e.g. supplied to a radiation detector 65 after passing through a band pass filter 31. The filter—detector means 31, 65 can also be replaced by a photoacoustic cell 68 filled with the gas type to be detected. The intensity modulation of the light source can either be carried out directly by controlling the operating current of the luminous body, or mechanically by a rotary or vibrating diaphragm, which is positioned between source 20 and detector cell 65.

FIG. 18 shows the use of the elliptical cylinder for illuminating the light entrance slit 66 of an optical device, e.g. a prism or grating monochromator. The lateral flat mirrors 57, 57', as shown in FIG. 10, have been omitted for ease of viewing purposes. The reflector is arranged in such a way that the slit surface coincides with the focal region of the reflector, as represented by 58'' in FIG. 10.

FIG. 19 relates to an example of the use of the covered paraboloid reflector, as shown in FIG. 13. The parallel light beam passing out of the reflector means 80, 40 is supplied to a gas cell 67, where part of the light is absorbed. The parallel beam is subsequently focused by means of focusing device 35 onto the light-sensitive surface of light detector 65. The absorption-caused attenuation of the light intensity is a measure of the gas concentration in gas cell 67, the monochromator element being designated 31.

FIG. 20 shows an example of a use of the covered hemiellipsoidal reflector 10', 40 of FIG. 5 for the photoacoustic detection of gases. The light beam passing out of opening 42 is supplied to a gas-filled photoacoustic cell 68. Reference is made in this connection to PCT Application No. CH 82/00026. The bundled light beam, which passes out of opening 42 in the flat mirror surface, initially strikes an optical band pass filter 31 and then passes into the photoacoustic cell 68. If the light beam is intensity-modulated, which is made possible e.g. by the alternating switching on and off of light source 20, the radiation absorbed by the gas in cell 68 leads to periodic pressure fluctuations, which are detected by microphone 69. It is appropriate for lengthening the light path to provide a flat or curved light reflector on the rear wall of photoacoustic cell 68. It is particularly advantageous to use a concave mirror 57, as shown in FIG. 20, which is adapted to the shape of the substituted ellipsoid half 10''. Thus, the unabsorbed portion of the radiation striking cell 68 can be returned to ellipsoidal reflector 10', 40 without varying the path of the beam. The consequence is an increase in the optical efficiency of the light collector.

Analogously to the representation of FIG. 20, FIG. 21 shows a photoacoustic measuring apparatus as a possible use of the elliptical cylinder. The photoacoustic measuring cell 68' is constructed cylindrically, which means a good utilization of the light. The shape of the concave mirror 57' can also be such that it supplements the elliptical cylindrical shape 50'' of the main reflector 50'. As a result, light which is not absorbed in the cell, can pass back to photoacoustic cell 68' after reflection in main reflector 50'.

Monochromatic light must be used for selected gas detection by means of the optical spectroscopic method. If a filament is used as the light source and which naturally emits light in a broad spectral range, a monochromator is necessary. A narrow band interference filter 31 is most suitable for our purposes. However, it is also conceivable to use a closed cell filled with a suitable gas which, as a result of the specific absorption bands of the gas (mainly in the infrared spectral region) is not transparent in certain spectral regions.

FIG. 22 shows the combination of a mechanical light modulator and a monochromator. Such a combination is particularly appropriate, because for measuring reasons the light intensity must in any case be modulated. At least one interference filter 33 or at least one gas cell 34 is arranged on the rotary disk 32. If several interference filters 33, 33', 33'', etc or cells 34, 34', 34'', etc are used with different gas fillings, or alternatively combinations of interference filters and gas cells, it is made simultaneously possible to separately determine several components of a gas mixture (further reference will be made thereto hereinafter).

Instead of using circular interference filters or gas cells, as shown in FIG. 22, it is also possible to use sector-shaped, joined filter elements.

As stated hereinbefore, compared with the extinction method, the photoacoustic gas measuring method has the advantage that the gas concentration determination does not result from the differential measurement of two intensities, but is instead directly obtained from the luminous efficiency absorbed in the gas cell. Thus, the intensity $I_o$ of the light source merely passes into the gas concentration measurement as a proportionality constant. In many cases, the natural stability of the light source is adequate for the accuracy of the measurement. However, it is occasionally desirable for the light intensity $I_o$ to be constantly monitored. For example, this $I_o$ measurement can take place by coupling out a partial beam not subject to the light absorption in the sample gas. This partial beam is supplied to a reference detector. It is a disadvantage of this arrangement that measuring and reference signals of different detectors are determined, which have different temperatures and pressure dependencies and different ageing characteristics. It is therefore desirable that both the measuring signal and the reference signal can be determined by the same detector. Such an arrangement would simultaneously offer the advantage of a reliable self-monitoring of the device.

FIGS. 23 and 24 show devices, which permit a combined measurement of the gas concentration and the light source intensity $I_o$. In the case of the device shown in FIG. 23, the combined measurement is achieved by a mechanical manipulation in the photoacoustic cell, whereas in the case of the device according to FIG. 24 the measuring process in the cell is of a purely optical nature. In both cases, the gas concentration measurement is based on the photoacoustic effect in gases, which has already been discussed in detail. However, the surface-specific photoacoustic effect is used for the light source intensity measurements. This is based on the fact that in the case of light absorption, the surface and the layer of air located immediately above it are heated. This heating of the air leads to an expansion and consequently in the case of a modulated light excitation to an alternating expansion and contraction of the air layer immediately above the light-absorbing surface. The resulting sound waves can be measured as a surface specific, photoacoustic signal. This signal, like the gas absorption-caused signal, is proportional to the light source intensity and can consequently be used for reference measurement purposes.

It must be ensured that there is no superimposing of the gas-specific, photoacoustic effect of the same gas by the gas-unspecific photoacoustic effect of the surface. The decoupling of the two effects can be achieved in that firstly a monochromator element, e.g. an interference filter 36 is placed in the path of the beam 14 and which is adapted to the light-absorbing gas type. It is simultaneously ensured that little light is absorbed by the absorber surface 37. Subsequently, a monochromator element 36' is placed in the beam path, whose transmission range does not coincide with the absorption range of the measuring gas in gas cell 68. Simultaneous measures ensure that the maximum amount of light is absorbed by absorber surface 37. Thus, by means of microphone 69, firstly the measuring gas concentration (FIGS. 23a and 24a) and then the light gas intensity (FIGS. 23b, 24b) are determined.

According to FIG. 23, the change from one measurement to the other is brought about by the filter change 36, 36' and an adjustment of plate 39 relative to absorber surface 37 which is parallel or transverse with respect to the incident light. A disadvantage of this arrangement is the mechanical interference in the photoacoustic cell 68.

The device shown in FIG. 24 is more advantageous from this respect. During the gas concentration measurement, the light beam 14 is guided as a laterally tightly defined bundle into the photoacoustic cell 68. Thus, a signal is measured at microphone 69 which corresponds to the gas concentration in cell 68. Then, alongside the monochromator element 36', a light beam-extending or a light beam-scattering element 38 is placed in the beam path, so that part of the light within the photoacoustic cell 68 strikes an e.g. circular disk 39', laterally of main beam 14, with absorber surface 37.

However, there is no need for the geometrical light beam changes by element 38 and the lateral arrangement of absorber surface 37 with respect to the light beam, if it is ensured that the measuring gas in cell 68 and the absorber surface 37 absorb light in preferably non-overlapping spectral regions and the monochromator elements 36, 36' are correspondingly chosen. In this case, the absorber surface 37 can be placed e.g. directly on the rear wall of photoacoustic cell 68. In this case, absorber surface 37 can be suitable as a selective light absorber, which reflects well in the infrared spectral region, but absorbs a large amount of light in the visible region.

The photoacoustic effect is based on the fact that the sound field is measured, which is formed in the gas cell by the absorption of intensity-modulated light radiation. Thus, the photoacoustic measuring device is sensitive from the outset to acoustic interference. It is therefore unavoidable to take corresponding sound-absorbing measures.

During the measurement, it must be ensured that the light absorption-caused sound signal is not attenuated by the escape of gas from the photoacoustic cell, whilst simultaneously preventing the penetration of external noise, which could increase the noise level of the measurement.

If working under a high light modulation frequency, it is possible to use elements constituting flow resistance means, such as narrow capillaries, gas filter disks, etc. However, in the case of low modulation frequencies, the use of efficient sound-absorbing means is unavoidable. Commercial mechanical valves ideally satisfy this condition from the technical standpoint, but they are relatively expensive and their control is complicated. Two possibilities of acoustic decoupling are described in Swiss Application No. 4,853/71-8 of 24.7.1981 and PCT Application No. CH82/00026 of 23.2.1982 which are based on hydrodynamic, acoustic decoupling.

FIG. 25 shows one of the possible realisations. Pump device 71 draws the gas outside the system via feed line 74 through the liquid medium 75 into container 76, from where it passes via connection 74" into photoacoustic cell 68. The gas discplaed from photoacoustic cell 68 passes via connection 74''' through liquid medium 75' into container 76, where it is pumped out via feed line 74'.

If pump device 71 is out of operation, as a result of the liquid media 75, 75', the photoacoustic cell is largely decoupled from the exterior, i.e. the photoacoustic cell is scarcely attenuated and the penetration of acoustic interfering signals is largely prevented. The acoustic decoupling of the photoacoustic cell is based on the fact that air and liquid media have very different acoustic stiffnesses (h=$\sqrt{E \cdot p}$, E: modulus of elasticity, p:density) and consequently the acoustic power matching to the gas—liquid and liquid—gas intersections is very poor. In the human ear, where this problem occurs during sound transmission from the outer ear to the perilymph of the inner ear, a good power adaptation is ensured by the auditory ossicles in the middle ear. The different acoustic stiffness of air and perilymph is taken into account by a mechanical transmission (transmission ratio 50:1).

Due to the gas only flowing intermittently through the liquid media 75, 75', when operating pump device 71, characteristic modulated pressure fluctuations recorded with microphone 69, occur in the photoacoustic cell 68. The resulting microphone signal makes it possible to check the operation of the flow system.

The liquid media 75, 75' simultaneously act as gas filters. They make it possible to wash the gas prior to the entry into the photoacoustic cell 68. Through a suitable choice of media 75, 75', it is also possible to remove from the gas to be measured certain measurement-impairing components (e.g. $H_2O$). For this purpose, it is also conceivable to connect by means of feed lines 74, 74', containers 76, 76' to further containers identical thereto and other gas treatment systems. In order to carry out an additional gas precleaning, media 75 and 75' can be replaced by solids.

FIG. 26 shows an additional measure making it possible to connect containers 76, 76', e.g. below the liquid media 75, 75' via feed line 77 to one or more further container 76'' containing reserves of media 75, 75', so that after a certain time the said media can be automatically replaced in 76 and 76', e.g. by valves 77'. This method is particularly advantageous when using several measuring cells.

FIG. 27 shows another embodiment of the invention. The liquid media 75, 75' are located in capillaries 78, 78'. The diameters of capillaries 78, 78' are such that in the case of identical pressure in expansion tank 78'' or 78''' and in outlet connection $78^{IV}$ or $78^{V}$, the capillary forces prevent an outflow of the liquid medium 75 in the range of the operating temperatures.

In outlet connection $78^V$, pump device 71 produces such a pressure drop, that the liquid medium 75 escapes out of capillaries 78 into expansion tank 78'' and the gas in outlet connection $78^{IV}$ passes via capillaries 78 into expansion tank 78'' and via feed line 74'' into photoacoustic cell 68. The gas displaced from photoacoustic cell 68 passes via feed line 74''' into expansion tank 78''', where it forces the medium 75' in capillaries 78' into outlet connection $78^V$ and it is pumped away.

If pump device 71 is switched off, the liquid medium 75 or 75' in expansion tank 78'' or outlet connection $78^V$ flows back into capillaries 78 or 78' and consequently decouples the photoacoustic cell 68 from the outside sound sources and simultaneously ensures the insulation of the photoacoustic pressure signal in the cell. Instead of fitting pump device 71 on outlet connection $78^V$, it can be fixed to outlet connection $78^{IV}$.

In order to prevent the penetration of media 75, 75' into cell 68 and to ensure the return flow into the corresponding capillaries, in the presently described arrangement, the cell need only be correctly positioned relative to gravity during the gas exchange phase and as shown in FIG. 27. Outside the gas exchange phases, e.g. during transport, measurement, etc, the mounting is of no importance due to the capillary forces acting in these intermediate phases, because it prevents the outflow of media 75, 75'.

Here again, microphone 69 can monitor the function of the flow device during the gas exchange, due to the resulting characteristically modulated pressure fluctuations in photoacoustic cell 68.

The above-described decoupling elements of FIGS. 25 and 27, which are based on hydrodynamic principles, have the disadvantage that the viscosity-caused, restricted temperature range and the fact that the photoacoustic cell can be contaminated by the aerosol formed during the flow of the measuring gas through the confining liquid. Through the choice of a suitable confining liquid and by introducing an aerosol filter, these disadvantages can be largely eliminated.

As an alternative to the hydrodynamic decoupling elements, FIGS. 28 and 29 show acoustic decoupling devices, which ensure a purely mechanical separation, but do not suffer from the high cost of solenoid valves.

FIG. 28 shows a modified form of a reed relay capsule, as used in electrical switches. Under the influence of the magnetic field which, with the excitation switched on, runs parallel to magnetizable spring 91, the latter is pressed against the also magnetizable counterpieces 92, the opening 93 in counterpiece 92 being closed. The seal 94 ensures acoustic separation. The counterpressure resistance of such a valve is only limited, because the pressure fluctuations of the photoacoustic signal are in the mPa range. However, the present valve satisfies the set requirements.

The acoustic decoupling device of FIG. 29 is very similar to that of FIG. 28. The maintaining of the spacing between part 94 and counterpiece 92', i.e. the control of the valve is carried out electrostatically by means of a piezoelectric element 95 and not mechanically.

It is finally stressed that it is important for the operation of the aforementioned light reflector means of FIGS. 1 to 21, that there is a retroreflector, which returns the light back to the source, that the light source for the emitted radiation is partly transparent and that the rear region of the reflector facing the light exist slit has a good reflectivity and is not covered by the source mount.

We claim:

1. An optical device for emitting a substantially parallel light beam bundle, comprising:
   a concave reflector having a plane of symmetry;
   a light source mounted at a focal point of said reflector and defining a source area;
   a retroreflector at least partially covering a concave portion of said reflector and arranged such that at least some light beams emitted from said light source are reflected back into said source area;
   an opening in said retroreflector at an intersection of said plane of symmetry and said retroreflector;
   mounting means for supporting said light source in said reflector, said mounting means intersecting said reflector at a location spaced from a point on said reflector in said plane of symmetry and opposite said opening; and
   a body influencing characteristics of irradiated light arranged between the light source and the retroreflector.

2. An optical device according to claim 1 wherein the reflector is elliptical and the retroreflector is flat.

3. An optical device according to claim 1 wherein the reflector is parabolic and the retroreflector is planar.

4. An optical device according to claim 2 wherein said reflector is a rotational ellipsoid; and said light source comprises a spot about said focal point.

5. An optical device according to claim 2 wherein said reflector is a rotational ellipsoid defined by a rotational axis; and said light source comprises a filament linear to said rotational axis.

6. An optical device according to claim 3 wherein said reflector is part of a rotational paraboloid; and said light source comprises a spot about said focal point.

7. An optical device according to claim 3 wherein said reflector is part of a rotational paraboloid with a rotational axis; and said light source comprises a filament linear to said rotational axis.

8. An optical device according to claim 2 wherein the reflector is an elliptical partial cylinder with a cylinder axis; and the light source is in a zone about a focal line linear to the cylinder axis.

9. An optical device according to claim 3 wherein the reflector is a parabolic partial cylinder with a cylinder axis and the light source is in an area about a focal line linear to the cylinder axis.

10. An optical device according to claim 1 wherein the reflector is one part of a rotational ellipsoid, the retroreflector being another part of the rotational ellipsoid; and the light source is a spot at a focal point of the rotational ellipsoid.

11. An optical device according to claim 1 wherein the reflector is part of an elliptical cylinder; the retroreflector is formed with the same elliptical curve as the reflector; and the light source is located in one area around two focal lines linear to a cylinder axis, the light source being a filament.

12. An optical device according to claim 1 wherein said light source is partially transparent.

13. An optical device for emitting a substantially parallel light beam bundle, comprising:
   a concave reflector having a plane of symmetry and being part of an elliptical cylinder;
   a light source mounted at a focal point of said reflector and defining a source area;
   a retroreflector at least partially covering a concave portion of said reflector and arranged such at at least some light beams emitted from said light source are reflected back into said source area, the retroreflector being formed with the same elliptical curve as the reflector;
   an opening in said retroreflector at an intersection of said plane of symmetry and said retroreflector;
   mounting means for supporting said light source in said reflector, said mounting means intersecting said reflector at a location spaced from a point on said reflector in said plane of symmetry and opposite said opening, the light source being located in one area around two focal lines linear to a cylinder axis and being a filament; and
   additional lateral reflectors coupled to the reflector at an angle to the cylinder axis.

14. An optical device according to claim 13 wherein the lateral reflectors extend adjacent the retroreflector and define a slit therebetween.

15. An optical device according to claim 13 wherein the lateral reflectors are planar and orthogonal to the cylinder axis.

16. An optical device according to claim 13 wherein the lateral reflectors are planar and are acutely angled to the cylinder axis.

17. An optical device according to claim 13 wherein the additional lateral reflectors are curved.

18. An optical device according to claim 17 wherein the lateral reflectors have a cylindrical-parabolic curvature.

19. An optical device according to claim 18 wherein there is a continuous transitional curvature from the elliptical cylinder to the lateral reflectors.

20. An optical device for emitting a substantially parallel light beam bundle, comprising:
   a concave reflector having a plane of symmetry;
   a light source mounted at a focal point of said reflector and defining a source area;
   a retroreflector at least partially covering a concave portion of said reflector and arranged such that at least some light beams emitted from said light source are reflected back into said source area;

an opening in said retroreflector at an intersection of said plane of symmetry and said retroreflector;

mounting means for supporting said light source in said reflector, said mounting means intersecting said reflector at a location spaced from a point on said reflector in said plane of symmetry and opposite said opening; and a body influencing characteristics of irradiated light arranged between the light source and the retroreflector, the retroreflector being elliptically curved.

21. An optical device according to claim 20 wherein the light-influencing body has light-refracting properties.

22. An optical device according to claim 21 wherein the light-influencing body has light-absorbing and partially reflecting properties.

23. An optical device according to claim 22 wherein the light-absorbing body is a cell filled with a measuring gas, feed lines with valves being connected to the cell to replace gas in the cell.

24. An optical device for emitting a substantially parallel light beam bundle, comprising:

a concave reflector having a plane of symmetry;

a light source mounted at a focal point of said reflector and defining a source area;

a retroreflector at least partially covering a concave portion of said reflector and arranged such that at least some light beams emitted from said light source are reflected back into said source area;

an opening in said retroreflector at an intersection of said plane of symmetry and said retroreflector;

mounting means for supporting said light source in said reflector, said mounting means intersecting said reflector at a location spaced from a point on said reflector in said plane of symmetry and opposite said opening; and a light-influencing body located in a light beam path extending through the opening in retroreflector.

25. An optical device according to claim 24 wherein the light-influencing body has light-absorbing and partly reflecting properties.

26. An optical device according to claim 25 wherein the light-influencing body is a cell filled with a measuring gas, feed lines with valves being connected to the cell to replace gas in the cell.

27. An optical device according to claim 25 wherein the light-influencing body has, alongside a light-absorbing medium, a device with a light-absorbing layer.

28. An optical device according to claim 27 wherein the light-influencing body is a gas cell and the light-absorbing medium is a gas.

29. An optical device according to claim 24 wherein a monochromatic element is located in the path of emitted light.

30. An optical device according to claim 29 wherein said monochromatic element is an optical band pass filter.

31. An optical device according to claim 24 wherein a light-refracting body is located in the path of emitted light.

32. An optical device according to claim 24 wherein a light-scattering body is located in the path of emitted light.

33. An optical device according to claim 24 wherein a light-diffracting body is located in the path of emitted light.

34. An optical device for emitting a substantially parallel light beam bundle, comprising:

a concave parabolic reflector having a plane of symmetry and being a parabolic partial cylinder with a cylinder axis;

a light source mounted at a focal point of said reflector and in an area about a focal line linear to the cylinder axis, and defining a source area;

a planar retroreflector at least partially covering a concave portion of said reflector and arranged such that at least some light beams emitted from said light source are reflected back into said source area;

an opening in said retroreflector at an intersection of said plane of symmetry and said retroreflector;

mounting means for supporting said light source in said reflector, said mounting means intersecting said reflector at a location spaced from a point on said reflector in said plane of symmetry and opposite said opening; and additional lateral reflectors coupled to the reflector at an angle to the cylinder axis.

35. An optical device according to claim 34 wherein the lateral reflectors extend adjacent the retroreflector and define a slit therebetween.

36. An optical device according to claim 34 wherein the lateral reflectors are planar and orthogonal to the cylinder axis.

37. An optical device according to claim 34 wherein the lateral reflectors are planar and are acutely angled relative to the cylinder axis.

38. An optical device according to claim 34 wherein the additional lateral reflectors are curved.

39. An optical device according to claim 38 wherein the lateral reflectors have a cylindrical-elliptical curvature.

* * * * *